United States Patent [19]

LeViness

[11] 4,219,800
[45] Aug. 26, 1980

[54] REMINDER FOR VEHICLE DRIVERS

[76] Inventor: Richard D. LeViness, 321 N. Division St., Salisbury, Md. 21801

[21] Appl. No.: 973,592

[22] Filed: Dec. 27, 1978

[51] Int. Cl.² ............................................. G08B 21/00
[52] U.S. Cl. .................................. 340/52 D; 340/576; 200/61.57
[58] Field of Search ...................... 340/52 D, 573, 575, 340/576; 200/61.57; 180/99

[56] References Cited

U.S. PATENT DOCUMENTS

| | | | |
|---|---|---|---|
| 3,585,626 | 6/1971 | Tartarini | 340/575 |
| 3,824,537 | 7/1974 | Albertson | 340/576 |

Primary Examiner—Alvin H. Waring
Attorney, Agent, or Firm—C. A. O'Brien; Harvey B. Jacobson

[57] ABSTRACT

A device for reminding vehicle drivers to continuously retain their conscious mind on the task of driving the vehicle which utilizes impulsive gripping of the steering wheel of the vehicle with an increased force resulting from stimulation of the adrenal cortex and secretion of adrenalin as fatigue or fear registers in the brain of the driver. The increase in the gripping force serves to close an electrical circuit to energize a reminder in the form of an illuminated message or sign in a flashing pattern for a predetermined time period after which an audible reminder is actuated thereby combining the senses of touch, sight and hearing to remind the driver to give full time and attention to driving the vehicle so that the driver's conscious mind is kept on the task of driving and the driver is warned of imminent danger, thereby avoiding a potential accident. A pair of pads are mounted on the steering wheel with each pad including an electrical switch which is operated in response to increased gripping force on the steering wheel to activate a reminder in the form of a sign or other indicator which may be illuminated in a flashing pattern and located in a position for easy observation by the vehicle driver.

6 Claims, 5 Drawing Figures

REMINDER FOR VEHICLE DRIVERS

BACKGROUND OF THE INVENTION

1. Field of the Invention

The present invention generally relates to a safety device for use with a vehicle such as an automobile, or the like, and more specifically to a reminder for a vehicle operator in the form of a signaling device or indicator operated in response to an increased gripping force exerted by the vehicle driver on the steering wheel or other control device for the vehicle to remind the driver to keep his/her conscious mind on the task of driving the vehicle.

2. Description of the Prior Art

Prior art devices have been invented for the purpose of keeping a vehicle driver awake with such devices frequently relying upon relaxation of the grip on the steering wheel by the vehicle operator to warn the vehicle driver that drowsiness or sleepiness is approaching, so that corrective action may be taken. The following U.S. patents, known to applicant, disclose various prior art devices of this general type:

U.S. Pat. Nos. 2,199,060—Apr. 30, 1940—Young
U.S. Pat. Nos. 2,237,607—Apr. 8, 1941—Rusche
U.S. Pat. Nos. 2,271,698—Feb. 3, 1942—Lofwall
U.S. Pat. Nos. 3,026,503—Mar. 20, 1962—Scheer
U.S. Pat. Nos. 3,049,090—Aug. 14, 1962—Bergen
U.S. Pat. Nos. 3,585,626—June 15, 1971—Tartarini.

U.S. Pat. No. 2,199,060 is a sleep inhibitor which discharges ammonia gas or the like toward the vehicle driver to awaken a drowsy or sleeping driver. U.S. Pat. No. 2,237,607 discloses an apparatus which actuates a bell when the steering wheel is improperly gripped. U.S. Pat. No. 2,271,698 discloses a device which results in the vehicle driver receiving an electrical shock if the vehicle driver becomes drowsy or sleepy and thus not properly grip the steering wheel. U.S. Pat. No. 3,026,503 discloses a device which measures palmar conductivity or resistance to actuate a signaling device when the grip on the steering wheel is loosened such as when drowsiness approaches. U.S. Pat. No. 3,049,090 discloses a device responsive to loosening of the vehicle driver's grip on the steering wheel to provide a signal, either visual and/or audible or an electric shock to awaken the driver. U.S. Pat. No. 3,585,626 discloses a pressure responsive device which requires periodic gripping of the steering wheel or a signal device will be actuated which would occur when the vehicle driver becomes sleepy and the driver fails to properly grip the steering wheel.

The above mentioned patents disclose devices which operate in response to drowsiness or sleepiness in which the grip of the vehicle driver on the steering wheel becomes relaxed or reduces and thus actuate a warning device to awaken the driver and warn him that corrective action should be taken to avoid operation of the vehicle under such conditions. While such devices may operate effectively for their purposes, none of the above-mentioned patents discloses an arrangement which will provide a reminder to a vehicle driver to keep his/her conscious mind completely and continuously on the task of driving the vehicle.

SUMMARY OF THE INVENTION

An object of the present invention is to provide a reminder to vehicle drivers to constantly and continuously keep their conscious mind on the task of driving the vehicle to enable vehicles to be driven in a safe manner resulting in the reduction of accidents involving the vehicle driver not maintaining proper manipulative control of the vehicle.

Another object of the invention is to provide a reminder in accordance with the preceding object in the form of a visually observable sign or other indicating device having a message imparted to the vehicle driver in response to increased gripping force being applied to gripping pads on the vehicle steering wheel.

A further object of the invention is to provide a reminder in accordance with the preceding objects in which the reminder also includes an audible signaling or indicating device which is actuated after the visual signaling device or indicator has been operative for a predetermined time period to further remind the driver to keep his/her conscious mind on the task of driving the vehicle.

Still another object of the invention is to provide a reminder in which increased grip on the steering wheel actuates the reminder with the increased grip occurring as a result of a neurological mechanism (pituitary hormone) which stimulates the adrenal cortex to secret adrenaline which causes the muscles in the hands to react so that the driver will grip the pads on the steering wheel in a more forceful manner, thus actuating the reminder. This impulsive reflex action of the driver of the vehicle alerts the driver to the imminent danger so that a potential accident can be avoided, thus resulting in safe operation of the vehicle.

Still another object of the invention is to provide a reminder for vehicle drivers in accordance with the preceding objects which is relatively inexpensive to manufacture and install, long lasting and dependable in operation and effective in enabling vehicles to be operated in a safe manner.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
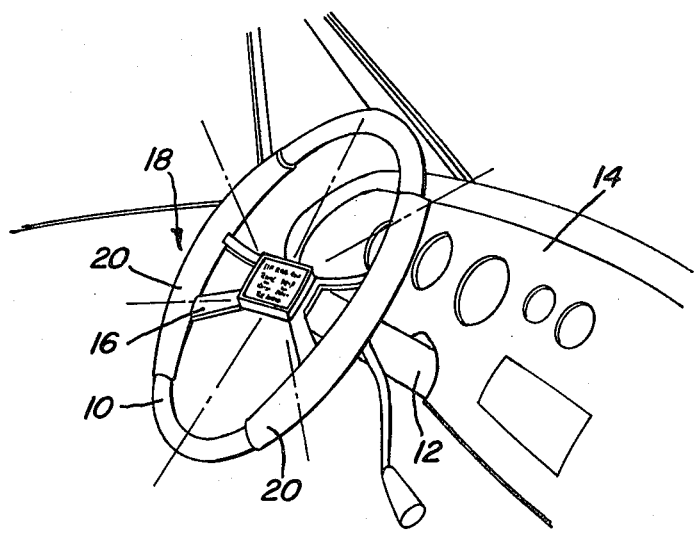
FIG. 1 is a fragmental perspective view of a vehicle steering wheel and associated structure illustrating the reminder of the present invention incorporated therein.

FIG. 1 illustrates the present invention installed in a conventional vehicle, such as an automobile, and which includes a steering wheel 10 mounted at the upper end of a steering column 12 which projects upwardly in an inclined manner in relation to a dashboard 14. The specific structure of the vehicle may vary depending upon the make and model of automobile, truck, bus, boat, motorcycle, airplane, train, construction equipment, or any other type of vehicle having a steering wheel or other control apparatus in which the driver or operator maintains a grip on the control apparatus in order to properly operate the vehicle. The steering wheel 10 is of conventional construction and includes a center cross arm or radial spokes 16 extending to a central hub area which is attached to the steering shaft within the steering column 12 in a conventional manner and which may include a horn actuating device associated therewith depending upon the make of automobile involved.

Figure 3:
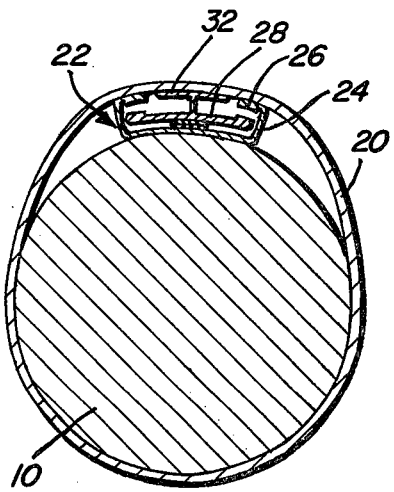
FIG. 3 is a transverse sectional view of one of the steering wheel pads illustrating the association of the grip responsive switch to the steering wheel and encircling sleeve.
Figure 4:
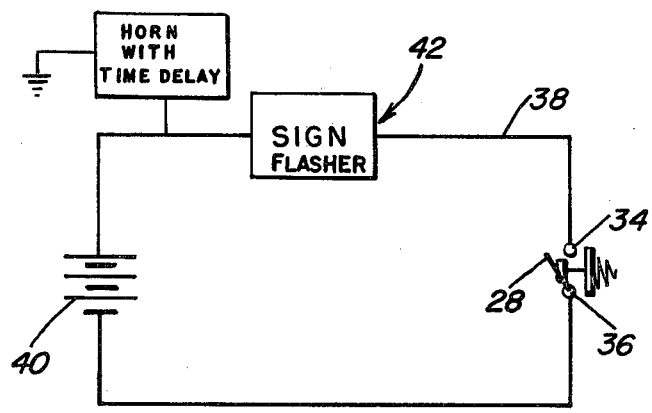
FIG. 4 is a schematic diagram of the electrical circuit for the reminder.
Figure 5:
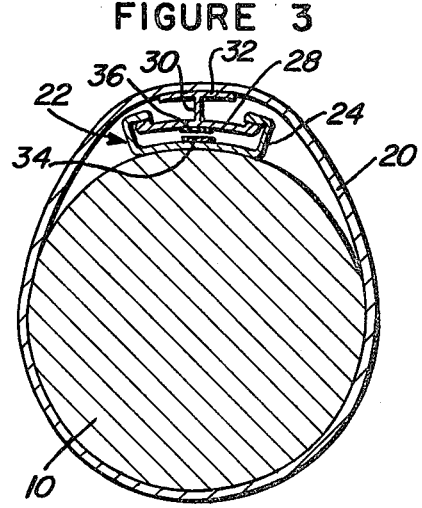
FIG. 5 is a sectional view similar to FIG. 3 but illustrating the grip responsive switch in its normal position.

At diametrically opposed points on the steering wheel 10, a gripping pad generally designated by numeral 18 is provided with the two pads 18 being oriented in the customary position at which the vehicle driver grips the steering wheel. Each gripping pad 18 includes a longitudinally elongated, tubular sleeve 20 constructed of flexible material such as plastic, rubber, leather, fabric, or the like, with the sleeve 20 having a transverse dimension greater than the steering wheel 10 as illustrated in FIGS. 3 and 4 with the ends of the sleeve being secured to the steering wheel in any suitable manner to prevent longitudinal shifting thereon and to form a closure for the interior of the sleeve 20. Also, the sleeve 20 may be permanently attached to the steering wheel in any suitable manner and to facilitate installation on the steering wheel, it may be provided with a line of separation longitudinally thereof which may be closed with any suitable type of closure, such as a slide fastener or other equivalent fastening devices. Disposed longitudinally within the sleeve 20 is a grip responsive switch generally designated by numeral 22 and including a longitudinally elongated channel-shaped member 24 fixedly attached to the exterior of the steering wheel 10 in any suitable manner with the outer edges of the flanges of the channel-shaped member 24 being inturned to define retaining flanges 26 for receiving and retaining a plate 28 within the channel-shaped member 24. The plate 28 includes a centrally disposed web 30 and a transversely arcuate pressure plate 32 at the outer edge of the web which underlies and engages and generally conforms with the inner surface of the sleeve 20 as illustrated in FIGS. 3 and 5. The sleeve 20 is constructed of a resilient, shape sustaining material having memory characteristics, such as plastic, and the pressure plate 32 is attached to the inner surface thereof so that the sleeve will return the plate 28 to its outermost position as limited by the flanges 26 when gripping pressure is not applied to the exterior of the sleeve 20. A return spring, such as a small coil compression spring or a series of longitudinal spaced springs, may be interposed between the bottom of the channel-shaped member 24 and the plate 28 to return the plate 28 to its outermost position when gripping forces is not applied to the gripping pad 18.

Electrical contacts 34 and 36, respectively, are attached to the channel-shaped member 24 and the plate 28 in opposed relation to each other so that the contacts will engage each other when the pressure plate 32 is moved inwardly such as when an increased gripping force is applied to the exterior of the sleeve 20 in the area of the pressure plate 32. The contacts 34 and 36 may be in the form of elongated strips connected in any suitable manner longitudinally along the channel-shaped member 24 and the pressure plate 28 and may be of any suitable conductive material with the channel-shaped member 24 and plate 28 being preferably constructed of plastic, or the like. Also, the contacts 34 and 36 are incorporated into an electrical circuit 38 including the vehicle battery 40 and a signaling device or indicator generally designated by numeral 42 in FIG. 4.

Figure 2:
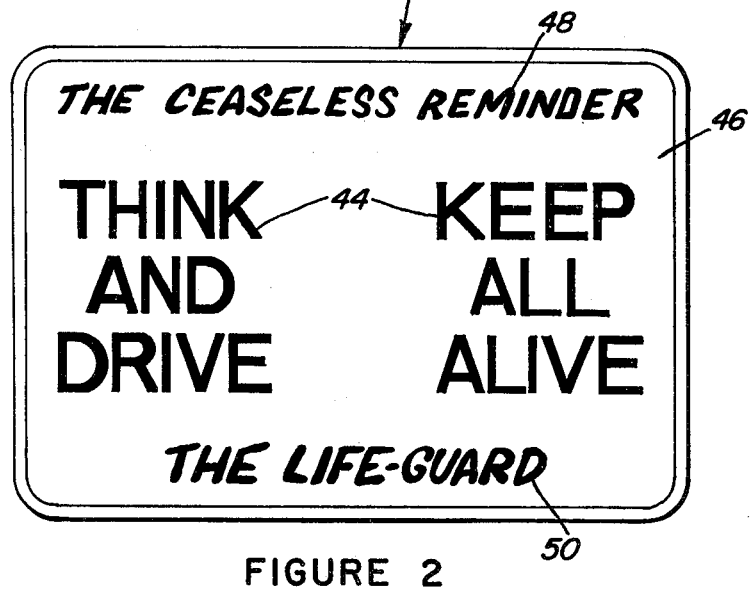
FIG. 2 is a plan view of the visual message observable by the vehicle operator to remind him to keep his conscious mind on the task of driving the vehicle.

The visual signaling device or indicator 42 includes indicia 44 mounted on a planar member 46 or the like to provide an appropriate message to the vehicle driver when the signaling device is observed. As illustrated in FIG. 2, the indicia 44 "THINK AND DRIVE—KEEP ALL ALIVE" appears in the manner illustrated and indicia 48 may be provided along the top edge of the panel 46 and indicia 50 along the bottom edge thereof which may be of a descriptive or fanciful nature, such as "THE CEASELESS REMINDER" and "THE LIFE-GUARD". The panel 46 may be conveniently mounted in the central hub portion of the steering wheel 10, as illustrated in FIG. 1, since many automobiles have a relatively large central hub area and the shape and configuration of the panel 46 may be varied to conform with the existing shape and configuration of the central hub area of the steering wheel. In some installations, it may not be appropriate to mount the panel 46 in the central area of the steering wheel and, in that event, the panel 46 may be mounted on the dashboard or in any other convenient location where it is readily observable by and generally in the line of sight of the vehicle driver. This panel 46 may be provided with a hollow interior with lighting in order to back light the indicia so that the indicia which may be transparent or translucent will be readily observable and the back lighting is preferably provided with a flasher so that the driver's attention will be directed to the message provided by the indicia. For normal day driving, the reminder remains unlighted because the message is clearly legible to the driver. For normal night driving, the reminder is illuminated and functions with the general electrical system and a suitable manual switch may be provided to let the driver selectively energize or deenergize the signaling device 42. In any event, during day or night driving, when a physiological change in the driver occurs, the result of the instinctive act of the driver exerting compulsive pressure on the grip pads 18 is the activation of the illuminated signaling device in a flashing pattern for a predetermined period of time, such as ten seconds, thus alerting the driver to imminent danger. Promptly following this initial ten second stage, the flashing pattern discontinues and the light in the signaling device remains constantly illuminated for another predetermined short period of time after which the horn on the vehicle is activated for a predetermined period of time, thus combining the senses of touch, sight and hearing for indicating imminent danger so that a potential accident may be avoided. Thus, the circumstances that produce the need for safety, at the same instant, places the preventive mechanism in the hands of the driver where it belongs rather than waiting until the driver becomes drowsy or sleepy before any warning is given. In almost any situation where the vehicle is being operated, the operator, at times, will let his conscious mind stray from the task of driving the vehicle and when this occurs, the driver substitutes the subconscious mind for the conscious mind and the vehicle, of course, has no way to remind the driver to keep his conscious mind on driving. The present invention provides such a reminder in the vehicle and constantly reminds the driver to keep his conscious mind on driving. The components of the signaling device 42 may be individually conventional with the arrangement being varied depending upon the requirements of each installation with the reminder being incorporated into vehicles as a factory installed or as an accessory for the after market.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A reminder for vehicle operators and the like having a manual control to keep their conscious mind continuously directed to the task of manipulating the manual control in a prescribed manner comprising a pressure responsive switch means associated with the manual control, and a signaling device located for easy observation by the operator, said signaling device being actuated in response to the switch means, said switch means being operative to actuate the signaling means in response to increase in gripping force exerted on the manual control by the operator, said manual control being a steering wheel, said switch means including a pair of gripping pads mounted at circumferentially spaced points on the steering wheel, each of said pads including a switch having a movable component movable to signaling device actuating position in response to increase in gripping force on a gripping pad.

2. The structure as defined in claim 1 wherein each pad includes a sleeve of resilient material mounted on the steering wheel and having an internal transverse dimension larger than the external transverse dimension of the steering wheel to provide a switch receiving space therebetween.

3. The structure as defined in claim 2 wherein said signaling device includes an illuminable sign having a reminder message thereon, flashing means connected with the sign, and an audible signal means actuated after a predetermined time period of increased gripping pressure on a gripping pad.

4. The structure as defined in claim 3 wherein said sign is mounted on the hub portion of the steering wheel, said audible signal means including a vehicle horn.

5. A reminder for operators of a manual control to keep their conscious mind continuously directed to the task of holding and manipulating the manual control in a prescribed manner comprising a gripping pressure responsive switch means associated with the manual control for grasping by the operator when holding the manual control, and a signaling device located for easy observation by the operator, said signaling device being actuated in response to the switch means, said switch means being operative to actuate the signaling means in response to increase in gripping force exerted on the manual control by the operator, said switch means including at least one gripping pad on the manual control, said pad including a switch having a movable component movable to signaling device actuating position in response to increase in gripping force on the gripping pad.

6. The structure as defined in claim 5 wherein said pad includes a sleeve of resilient material mounted on the manual control and having an internal transverse dimension larger than the external transverse dimension of the control to provide a switch receiving space therebetween, said signaling device including an illuminable sign having a reminder message thereon, flashing means connected with the sign, and an audible signal means actuated after a predetermined time period of increased gripping pressure on the gripping pad.

* * * * *